US009371596B2

(12) United States Patent
Faure et al.

(10) Patent No.: US 9,371,596 B2
(45) Date of Patent: Jun. 21, 2016

(54) METHOD FOR STRUCTURING A SURFACE USING COLLOIDAL PARTICLES IN AN ELECTRIC FIELD, RESULTANT SURFACES AND USES THEREOF

(75) Inventors: Chrystel Faure, Saint Selve (FR); Damien Bazin, Bordeaux (FR)

(73) Assignee: CENTRE NATIONAL DE LA RECHERCHE, Paris (FR)

( * ) Notice: Subject to any disclaimer, the term of this patent is extended or adjusted under 35 U.S.C. 154(b) by 226 days.

(21) Appl. No.: 14/002,288

(22) PCT Filed: Mar. 1, 2012

(86) PCT No.: PCT/FR2012/050427
§ 371 (c)(1),
(2), (4) Date: Nov. 4, 2013

(87) PCT Pub. No.: WO2012/117205
PCT Pub. Date: Sep. 7, 2012

(65) Prior Publication Data
US 2014/0050885 A1 Feb. 20, 2014

(30) Foreign Application Priority Data
Mar. 3, 2011 (FR) ..................... 11 51745

(51) Int. Cl.
C25D 13/20 (2006.01)
C25D 13/22 (2006.01)
C25D 5/02 (2006.01)
G01N 27/327 (2006.01)
C25D 5/18 (2006.01)

(52) U.S. Cl.
CPC ................ C25D 13/20 (2013.01); C25D 5/022 (2013.01); C25D 13/22 (2013.01); G01N 27/327 (2013.01); C25D 5/18 (2013.01); Y10T 428/24331 (2015.01)

(58) Field of Classification Search
CPC .......................................... C25D 13/00–13/24
See application file for complete search history.

(56) References Cited

U.S. PATENT DOCUMENTS 5,855,753 A * 1/1999 Trau ....................... C25D 13/18
204/484
2003/0102222 A1* 6/2003 Zhou ..................... B82Y 30/00
205/109
2011/0171137 A1 7/2011 Elnathan et al.

OTHER PUBLICATIONS

Search Report Dated 2012.
Bayati et al. "An Approach to Fabrication of Metal Nanoring Arrays." Dated: Jan. 28, 2010.
Valsesia et al. "Selective Immobilization of Protein Clusters on Polymeric Nanocraters." Dated: May 4, 2006.

* cited by examiner

Primary Examiner — Harry D Wilkins, III
Assistant Examiner — Ho-Sung Chung
(74) Attorney, Agent, or Firm — Sofer & Haroun, LLP

(57) ABSTRACT

A method of preparing inorganic and/or organic surfaces includes organized micro- or nanostructures using colloidal particles in an electric field, to the micro- or nanostructured surfaces obtained by application of this method, as well as to the various applications of these structured surfaces, notably in the field of photonics, catalysis, magnetic storage or biosensors.

13 Claims, 7 Drawing Sheets a                                      b a b c

| 30 µm | 10 µm | 3 µm |
| a | b | c |

(a)  (b)

y: 10.0 μm    x: 10.0 μm

METHOD FOR STRUCTURING A SURFACE USING COLLOIDAL PARTICLES IN AN ELECTRIC FIELD, RESULTANT SURFACES AND USES THEREOF

RELATED APPLICATIONS

This application is a National Phase Application of PCT/FR2012/050427, filed on Mar. 1, 2012, which in turn claims the benefit of priority from French Patent Application No. 11 51745 filed on Mar. 3, 2011, the entirety of which are incorporated herein by reference.

BACKGROUND

1. Field of the Invention

The present invention relates to a method of preparing inorganic and/or organic surfaces comprising organized micro- or nanostructures, to the micro- or nanostructured surfaces obtained by application of this method, and to the various applications of these structured surfaces, notably in the area of photonics, catalysis, magnetic storage or biosensors.

2. Description of Related Art

Methods of preparing nanostructured surfaces, i.e. more generally surfaces comprising organic or inorganic nanostructures, are the object of constant research, as these surfaces have varied applications depending on the nature and morphology of they nanostructures.

Surfaces covered with organized metallic nanostructures find applications in emerging fields such as nanophotonics, or as a substrate for surface-enhanced Raman spectroscopy (SERS). One of the properties of these surfaces is to increase the Raman signal obtained by several orders of magnitude, hence their interest in the analytical and bio-analytical industry for biosensors. In fact, when metallic structures are sufficiently close together, their surface plasmons can then be coupled, generating electromagnetic "hot spots" responsible for the signal enhancement effect. The distance between these structures is therefore a crucial parameter requiring fine control.

Arrays of polymer nanostructures are designed essentially for biotechnology applications, the nanostructures serving as anchoring points for biomolecules such as oligonucleotides for DNA chips, or proteins, notably enzymes, for biosensors. One of the difficulties is that these nanostructures must be separated by a matrix, on which the biomolecules that are to be anchored specifically on the nanostructures cannot become attached. When the polymer used for fabricating the nanostructures is an electrically conducting polymer, such as a polypyrrole for example, the arrays can then have applications as micro-/nano-electrodes.

Nanostructured surfaces can basically be prepared according to two broad types of techniques: "sequential" techniques and "parallel" or "masking" techniques.

According to the "sequential" technique, the nanostructures are deposited on the surface of a substrate point-by-point by scanning the surface with sophisticated apparatus of the microscope tip type (electron or atomic force or tunnel-effect) or with an ion or electron beam. These techniques are expensive, time-consuming and require considerable know-how. Conversely, the sizes obtained are small, of the order of a few nanometers.

According to the "parallel" technique, deposition is carried out on a surface that has been masked beforehand. The masks most widely used are of porous alumina as the size of the pores and their spacing can be controlled during manufacture. Nevertheless, this method is still time-consuming as it requires two steps for synthesis of the mask, as well as several steps for deposition of the metal, for example by electron beam evaporation, vacuum evaporation or else electrolytically, then a step of removal of the mask to obtain the anticipated array of nanodots. Moreover, this method has risks of notable chemical contamination.

An alternative to using these porous masks is to use colloidal lithography. For example, notably in the article of Bayati M. et al., Langmuir, 2010, 26(5), 3549-3554, a method has already been proposed for fabricating surfaces comprising metal (gold, platinum, copper) nanorings, consisting of covering the surface of a substrate, on which deposition is to be effected, with a dispersion of polystyrene beads, which will self-organize in a monolayer on the surface of said substrate, then, after evaporation of the solvent (water), covering the substrate with a solution of a metal precursor (metal salt) so that the precursor infiltrates, by capillarity, the spaces left free between the polystyrene beads. After reduction of the metal salt to cause fixation of the metal on the surface, the substrate is rinsed, then the polystyrene beads constituting the mask are removed by treatment with chloroform. A metal deposit is thus obtained that is either in the form of nanodots if the time of impregnation with the solution of metal salt was long, or in the form of nanorings if the time of impregnation with the solution of metal salt was short. However, this method is time-consuming in application and does not allow the morphology and size of the deposits obtained to be modulated with high precision.

The use of masks consisting of an array of colloidal particles has also been envisaged for preparing nanostructured surfaces with an array of polymer dots. Thus, Valsevia et al. (Adv. Func. Mat., 2006, 16, 1242-1246) propose for example a method of surface nanostructuring consisting of depositing a layer of polymer (polyacrylic acid: PAA) by the technique of plasma-enhanced deposition on a substrate, then depositing, by spin-coating on said layer of polymer, a layer of colloidal spheres in the form of a compact hexagonal array. The method then comprises a step during which these spheres are abraded under plasma in order to reduce their size, then an additional step makes it possible to deposit another polymer (polyethylene glycol: PEG) on these spheres and on the layer of PAA that has been made accessible by abrasion of the colloidal spheres. Finally, the spheres are removed, revealing PAA dots organized in a hexagonal array in a matrix of PEG According to this method, the size of the PAA dots is controlled by the size of the spheres and the abrasion time, parameters which also allow control of the distance between the dots. This method is therefore complex and requires multiple steps, as well as expensive equipment.

Currently, no method exists that allows nanostructured surfaces with controlled morphology, thickness and roughness to be obtained simply, in an easily modulated manner, inexpensively and in a minimum of steps.

Objects and Summary

The inventors therefore set themselves the goal of developing a method for producing such surfaces.

The present invention therefore relates to a method of preparing a nanostructured surface with inorganic and/or organic organized nanostructures, said method employing colloidal particles and an electrochemical cell comprising a positive electrode and a negative electrode, said electrodes being plane-parallel relative to one another, with conducting faces opposite each other, and separated from one another by an insulating spacer having at least two openings and delimiting a free volume (V) between the two electrodes, said method being characterized in that it comprises the following steps:

i) preparing a dispersion of electrically charged, monodispersed hydrophilic colloidal particles (particles P1) in an aqueous phase, said particles P1 having a size greater than or equal to about 0.5 µm;

ii) preparing a dispersion of electrically charged colloidal particles (particles P2) in an aqueous phase, said particles P2 having a size less than that of the particles P1, being of the same electric charge as the particles P1, and optionally containing at least one electrochemical species;

iii) introducing the dispersion of particles P1 into the free volume (V) through one of the openings in the spacer;

iv) causing the particles P1 to migrate toward the surface of the electrode of charge opposite to that of the particles P1 (working electrode), by applying a sinusoidal electric field perpendicularly to said electrodes, v) applying a sinusoidal electric field of decreasing frequencies at constant potential, to cause aggregation of the particles P1 on the surface of the working electrode;

vi) gradually increasing the frequency until a crystal lattice is obtained consisting of a monolayer of particles P1 on the surface of the working electrode;

vii) immobilizing the particles P1 in the form of said crystal lattice, by superimposing, on the sinusoidal electric field, a continuous electric field of sign opposite to the charge of the particles P1, then extinguishing the sinusoidal electric field while maintaining the continuous electric field for a sufficient time to cause adhesion of the particles P1 on the surface of the working electrode;

viii) introducing the dispersion of particles P2 into the free volume V of the electrochemical cell, and applying a continuous electric field for a sufficient time to cause migration and fixation of the particles P2 on the free surface of the working electrode on which the organized array of particles P1 has formed, and when the particles P2 contain an electrochemical species, oxidation or reduction of said electrochemical species on the surface of the working electrode;

ix) removing the particles P1 from the surface of the electrode to obtain a surface that is nanostructured with the particles P2 or with the oxidized or reduced electrochemical species supplied by the particles P2.

Moreover, the method of preparing these surfaces offers the following advantages:

it is rapid, simple and inexpensive to apply, since it only requires a small amount of raw material (particles), and does not require any heavy or high-tech equipment, a simple voltage generator sufficing;

it does not require special qualification, as the techniques used are simple to apply;

it allows nanostructuring on large areas, i.e. areas of several cm$^2$;

it is easy to modulate: variation of the electrical parameters at the voltage generator, of the concentration of colloidal particles P1 and/or P2 and of the duration of application of the electric fields makes it possible to obtain varied surface nanostructuring (varied morphology: holes, rings, and varied organization: hexagonal arrays, whether or not compact; triplets of particles P1 isolated from one another, said triplets being arranged in rods (spheres of particles P1 fused together three by three along a longitudinal axis) and/or in triangles);

it is polyvalent, in that it allows nanostructured surfaces to be obtained by deposition of metal or by deposition of polymer, and can notably be in the form of nanoholes or nanorings;

it is not harmful to the environment, nor is it dangerous since it only uses weak electric fields and no organic solvent;

the risks of contamination by the surroundings are minimized since all the steps take place in a "closed" environment fin the cell).

According to a preferred embodiment of the invention, the particles P1 are selected from spherical particles with average diameter between about 0.5 µm and 5 µm.

The particles P1 are preferably polymer spheres surface-functionalized with anionic groups such as for example sulfate, carboxylate or phosphate groups or with cationic groups such as for example ammonium groups.

According to a preferred embodiment of the method according to the invention, the particles P1 are polystyrene spheres surface-functionalized with sulfate groups.

The quantity of particles P1 in the dispersion preferably varies from about 0.1 to 0.6 wt %, or, for particles having a density of 1, from about $3 \times 10^8$ to $5.75 \times 10^9$ particles/mL. This quantity of particles is sufficient to cover an area of 2 cm$^2$. This quantity can be adjusted as a function of the crystal lattice of particles P1 that we wish to produce on the working electrode. The quantity of particles P1 in the dispersion must allow, as a maximum, a monolayer of particles to be deposited on the surface. With this limit, the larger the quantity of particles P1 in the dispersion, the more the surface will be covered uniformly and the denser will be the crystal lattice formed at the end of step v) for a given surface area, The particles P2 can constitute the deposit or can serve as carrier for an electrochemical species that will constitute the deposit after reaction on the electrode.

Thus, according to a first embodiment of the method according to the invention, the particles P2 constitute the deposit and are selected from filled polymers having at least one organic function having affinity for the working electrode, the metal particles surface-functionalized with at least one organic function having affinity for the working electrode and the carbon nanotubes surface-functionalized with at least one organic function having affinity for the working electrode.

In the sense of the present invention, "organic function having affinity for the electrode" means any function permitting fixation of the particles P2 on the surface of the working electrode. These functions are in particular selected from groups having at least one thiol function and the nitrogen-containing functions such as amino groups, for example hexamethyldiamine or diamine octane, and cyclic groups in which the nitrogen atom or atoms form an integral part of the ring such as the 1,4,8,11-tetraazacyclotetradecane group (also known by the trade name Cyclam®) or a thionine salt such as thionine acetate.

As particles P2 constituting the deposit, we may mention in particular particles of poly(styrene, divinylbenzene) surface-functionalized with nitrogen-containing groups such as 1,4, 8,11-tetraazacyclotetradecane, particles of polystyrene surface-functionalized with molecules of hexamethyldiamine, gold particles surface-functionalized with thiol-polyethylene glycol-amine or with dithiol-octane or with diamine-octane and carbon nanotubes surface-functionalized with thionine acetate.

According to a second embodiment of the method according to the invention, the particles P2 do not constitute the deposit but serve as carrier for an electrochemical species that will constitute the deposit after reaction on the electrode. According to this variant, the particles P2 are then preferably selected from lamellar vesicles based on at least one surfactant and containing said electrochemical species.

"Lamellar vesicles based on at least one surfactant" means, in the sense of the present invention, vesicles comprising at least one wall in the form of a bilayer containing at least one surfactant. There is abundant literature devoted to lamellar vesicles, often called unilamellar, paucilamellar or multilamellar vesicles depending on whether they comprise one, a limited number or a large number of bilayers of surfactant, respectively. Liposomes and niosomes are examples of surfactant-based lamellar vesicles.

According to a preferred embodiment of the invention, the particles P2 consist of multilamellar vesicles with an onion-like structure, i.e. of vesicles of roughly spherical shape consisting of a succession of concentric bilayers.

The charge carried by the particles P2 will of course determine which electrode will be used as the working electrode. Thus, during application of the continuous electric field, the vesicles bearing a positive charge will migrate to the surface of the working electrode performing the function of cathode, and conversely, the vesicles bearing a negative charge will migrate to the surface of the working electrode performing the function of anode.

The electrochemical species contained in these vesicles is preferably selected from metal ions and redox monomers. As metal ion, we may mention in particular cupric ions, lead, nickel, cadmium, cobalt, ferric, zinc ions etc. As redox monomer, we may mention in particular pyrrole, aniline and thiophene.

Such vesicles are described for example in international application WO 00/08237.

The size of the lamellar vesicles used according to the invention can vary over a wide range provided that they nevertheless have a diameter less than that of the particles P1. According to a preferred embodiment of the invention, the lamellar vesicles have a size between 0.1 µm and 1.5 µm.

The quantity of particles P2 in the dispersion preferably varies from 1 to 60 wt %, and even more preferably from 5 to 50 wt %, This quantity can be adjusted in relation to the thickness and morphology of the deposit that we wish to obtain on the surface of the electrode. Thus, when the quantity of particles P2 is large, of the order of 50 wt % in the water, rings are obtained that form around the particles P1. The thickness of the deposit between the rings and the ring height both increase with the time of application of the continuous electric field and therefore with the quantity of particles P2 attracted. When the quantity of particles P2 is small, of the order of 5 wt % in the water, the deposit comprises holes that have formed under the particles P1. The diameter of these holes, like that of the rings, depends notably on the diameter of the particles P1.

The dispersions P1 and P2 can easily be introduced into the free volume of the electrochemical cell, for example by means of a syringe.

The frequency of the sinusoidal electric field applied during step iv) preferably varies from 8 to 4 kHz.

According to a particular embodiment, the electric field applied, during step iv) between the two electrodes preferably varies from 100 to 150 V/cm and the crystal lattice of particles P1 is then a hexagonal array.

According to another particular embodiment, the electric field applied during step iv) between the two electrodes varies from 200 V/cm to 250 V/cm and the crystal lattice of particles P1 is then an array in the form of chains consisting on average of 3 particles P1.

The duration of step iv) generally varies from about 15 to 90 min. For a given frequency of electric field, this duration is selected as a function of the particle size. The smaller the particles, the longer said duration.

According to a preferred embodiment of the invention, the frequency of the electric field during step v) gradually decreases from 5 to 0.4 kHz, in successive stages with a duration varying independently from about 20 to 2 min.

Still according to a preferred embodiment of the invention, the frequency of the electric field during step vi) gradually increases from 0.4 to 1.6 kHz, in successive stages with a duration varying independently from about 20 to 2 mm.

The crystal lattice of particles P1 obtained on the surface of the working electrode at the end of step vi) can be in the form of a compact hexagonal array, a noncompact hexagonal array or in the form of an array consisting of an assemblage of particles P1, generally of triplets of particles P1 isolated from one another, said triplets being arranged in rods (spheres of particles P1 fused together three by three along a longitudinal axis) and/or in triangles. It should be noted that at the end of step v), the particles P1 are already organized in the form of a crystal lattice but the distance between particles is as small as possible (in contact, most often). It is the gradual increase in frequency during step vi) that will then make it possible to move the particles apart until the expected array is obtained.

During step vii), the continuous electric field is preferably applied with a potential difference varying from 40 to 100 V/cm.

The duration of step vii) preferably varies from 0.1 to 5 s.

During step viii), the continuous electric field is preferably applied with a potential difference varying from 80 to 120 V/cm.

The duration of step viii) preferably varies from 5 to 30 min.

The particles P1 can easily be removed, for example by rinsing with water or by means of an organic solvent such as tetrahydrofuran (THF) or by applying and then detaching an adhesive tape on the surface of the working electrode. Of course, during removal of the particles P1, a person skilled in the art will take care that the technique used does not also lead to removal of the particles P2 or of the oxidized or reduced electrochemical species that was supplied by the particles P2.

The nanostructured surfaces obtained by the method defined above are ready to be used directly after step ix) of removal of the particles P1.

Thermal treatments intended to induce fusion of particles P2 to obtain a continuous matrix can be carried out when the particles P2 are of a polymeric nature for example.

It is also possible to proceed to an additional step of functionalization of the nanostructured surface, for example with biomolecules of interest such as proteins or nucleic acids (oligonucleotides, DNA).

Thus, according to a particular embodiment of the invention, the method according to the invention further comprises, after step viii) of fixation of the particles P2, an additional step of functionalization of the particles P2 with a biomolecule of interest. Said additional functionalization step can in particular be carried out either just after step viii) of fixation of the particles P2 and before step ix) of removal of the particles P1, or after step ix) of removal of the particles P1.

According to a first embodiment of this variant, the particles P2 possess metal ions on the surface, notably when the particles P2 are surface-functionalized with nitrogen-containing groups such as 1,4,8,11-tetraazacyclotetradecane which have the property of complexing the divalent metal ions such as nickel or zinc and can then be functionalized with biomolecules bearing a histidine group. In this case, the step of additional functionalization of the particles P2 with a biomolecule can be carried out by simply contacting the surface bearing the particles P2 with a solution of the biomolecule in a buffer. The duration of contacting (incubation) is in this case about 1 hour. After incubation of the solution of biomolecule, the surface is then rinsed, for example with a buffer solution.

According to a second embodiment of this variant, the particles P2 are particles previously surface-functionalized with a streptavidin or biotin group or with an antibody. In this case, the particles P2 can serve for specifically binding the proteins respectively bearing biotin or avidin ligands or the antigen corresponding to the antibody.

Finally, according to a third embodiment of this variant, the particles P2 bear positive surface charges. In this case, they can be functionalized with DNA or oligonucleotides by electrostatic affinity.

As an example, these biomolecules of interest can be selected from all proteins bearing a histidine label, a streptavidin ligand or a biotin ligand, antigens, molecules of nucleic acids such as oligonucleotides and DNA.

The nanostructured surface obtained according to the method described above constitutes another object of the invention. It is characterized in that it is in the form of a surface functionalized with an organized array of particles P2 or with the reduced or oxidized electrochemical species transported initially by the particles P2.

More particularly, such surfaces can be in the firm of insulating surfaces comprising an organized array of electrically conducting holes, said holes having a diameter from 300 nm to 1.5 µm and being spaced apart by from 1 to 4 µm (center-to-center distance between holes). They can also be in the form of a film of the reduced or oxidized electrochemical species, said film having holes, metal rings or shells with a diameter varying from 300 nm to 1.5 µm, spaced apart by from 1 to 4 µm (center-to-center distance between holes). When the surface is in the form of an organized array of metal rings, their height varies from 25 to 160 nm.

According to a particular embodiment of the invention, the surface is functionalized with one or more biomolecules of interest, as defined above.

The nanostructured surfaces can have various applications depending on the nature of the particles P2 used or the nature of the electrochemical species transported by the particles P2.

Thus, according to a first embodiment, the invention also relates to the use of a surface obtained by the method according to the invention using, as particles P2, filled polymers having at least one organic function having affinity for the working electrode, for molecular detection in biotechnology (in the pharmaceutical industry for example). These surfaces can also be used as masks for other deposits in the holes left empty by the particles P1.

According to another embodiment, the invention relates to the use of a surface obtained by the method according to the invention using, as particles P2, lamellar vesicles transporting metal ions, and the deposit made on the surface of the working electrode is then of a metallic nature (metal nanorings for example), and the surfaces obtained can be used in photonics, in catalysis, in magnetic storage, as super-hydrophobic transparent surfaces, for the manufacture of biosensors, for optical detection, etc.

DETAILED DESCRIPTION

Surfaces nanostructured with copper can also find application for limiting the formation of biofilms (antibacterial effect of copper).

The present invention is illustrated by the following practical examples, but it is not limited to these.

EXAMPLES

Figure 1:
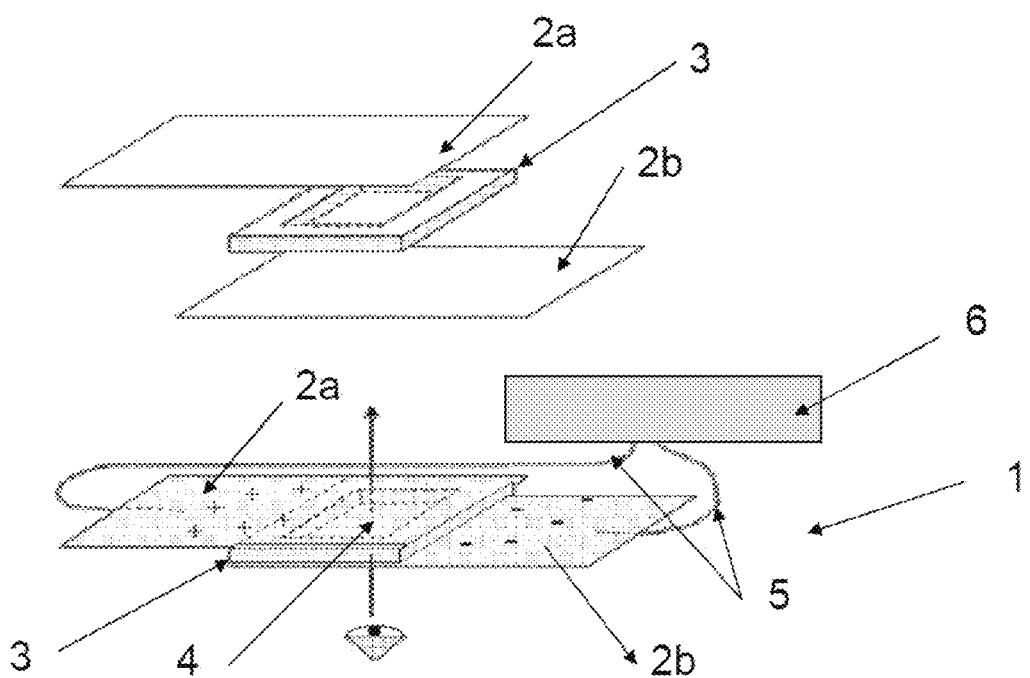
FIG. 1 shows various experiments of nanostructuring of surfaces presented in the examples carried out in an electrochemical cell, in accordance with one embodiment.

The various experiments of nanostructuring of surfaces presented in the examples given hereunder were carried out in an electrochemical cell (1) as shown schematically in the accompanying FIG. 1, consisting of two plane-parallel electrodes (2a, 2b) (glass plates coated with a film of ITO (indium-tin oxide) with a thickness of the order of about a hundred angströms), having the following dimensions 25 mm×50 mm and a thickness of 0.5 mm. These two electrodes (2a, 2b) rest on one another, with conducting faces opposite each other, and are spaced apart by a distance of 250 µm by an insulating seal (3) of square or circular shape made of polytetrafluoroethylene (PTFE), having two openings (not shown) for introducing the dispersions of colloidal particles P1 and P2 into the volume (4) delimited by the insulating seal (3) once in position between the two electrodes (2a, 2b). The two electrodes (2a, 2b) are connected by conducting wires (5), such as copper wires, to the positive and negative terminals of a voltage generator (6).

Example 1

Preparation of a Surface Nanostructured by a Polymer Matrix Having Holes According to the Method According to the Invention In this example, surfaces were prepared that were nanostructured by a polymer matrix having electrically conducting holes having a diameter of about 1.1 μm, 630 nm and 445 nm, thus creating an array of micro- or nano-electrodes.

1) First Step: Preparation of a Reverse Mask of Colloidal Particles P1

50 μl of an aqueous dispersion of particles P1-*a* at 0.1 wt %, consisting of polystyrene beads with a diameter of 2 μm, surface-functionalized with sulfate groups, sold under the trade name Polybeads® (and already functionalized) by the company Polysciences Inc., was introduced into the cavity of an electrochemical cell using a micropipette.

This dispersion was left to sediment for 20 minutes in a sinusoidal electric field (frequency: 5 kHz, 120 V/cm). The sequence shown in Table I below was then applied for organizing the particles P1 and immobilizing them on the positive electrode in a noncompact hexagonal array:

TABLE I

| Time | Frequency (kHz) | AC potential difference (V) | DC potential difference (V) |
| --- | --- | --- | --- |
| 20 min | 5 | 3 | — |
| 2 min | 4 | 3 | — |
| 2 min | 3 | 3 | — |
| 2 min | 2 | 3 | — |
| 2 min | 1.8 | 3 | — |
| 2 min | 1.6 | 3 | — |
| 2 min | 1.4 | 3 | — |
| 2 min | 1.2 | 3 | — |
| 2 min | 1 | 3 | — |
| 2 min | 0.9 | 3 | — |
| 2 min | 0.8 | 3 | — |
| 2 min | 0.9 | 3 | — |
| 2 min | 1 | 3 | — |
| 2 min | 1.2 | 3 | — |
| 1 s | 1.2 | 3 | 1 |
| 20 min | — | — | 2.3 |

A hexagonal array of colloidal particles P1-*a* was obtained having a characteristic spacing of 4.0 μm from center to center.

The experiment was then continued by lowering the frequency to 400 Hz while maintaining the potential difference at 3 V.

Figure 2:
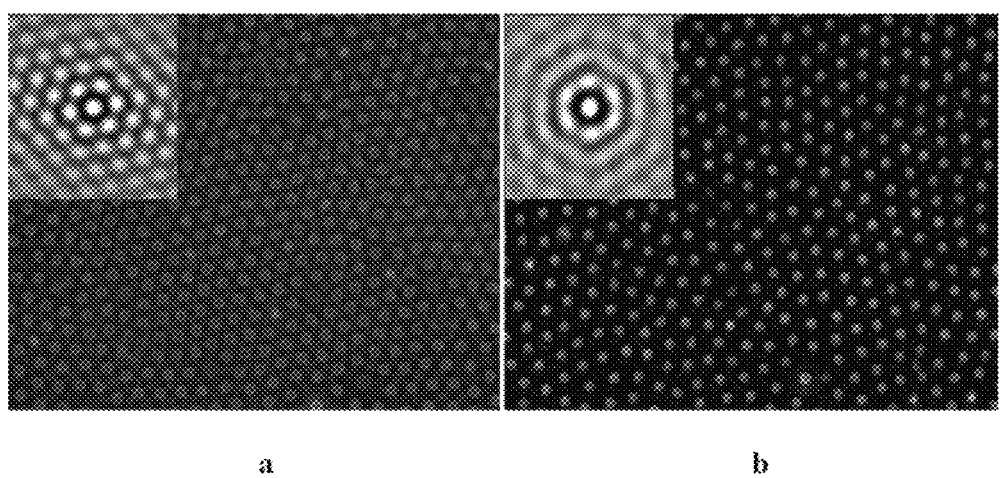
FIG. 2 is a photograph obtained by phase-contrast optical microscopy of the surface of the electrode according to Example 1, in accordance with one embodiment.

The accompanying FIG. 2 is a photograph obtained by phase-contrast optical microscopy (magnification ×630) of the surface of the electrode having the hexagonal array of colloidal particles P1-*a*, the center-to-center distance of which is fixed by the frequency of the sinusoidal electric field. In FIG. 2*a*) the particles are organized as a compact hexagonal array (in the case when the experiment was to continued as far as a final frequency=400 Hz), and in FIG. 2*b*) they are organized as a noncompact hexagonal array (final frequency=1200 Hz, Table 1).

A similar experiment was carried out using polystyrene beads P1-*b* and P1-*c* with diameter of 3 μm and of 1 μm respectively, surface-functionalized with amine groups, sold under the trade name Polybeads® (and already functionalized) by the is company Polysciences Inc.

The electrical sequences applied for organizing the beads P1-*b* and P1-*c* are given below in Tables II and III respectively:

TABLE II

| Time | Frequency (kHz) | AC potential difference (V) | DC potential difference (V) |
| --- | --- | --- | --- |
| 20 min | 5 | 3 | — |
| 2 min | 2.5 | 3 | — |
| 2 min | 2 | 3 | — |

TABLE II-continued

| Time | Frequency (kHz) | AC potential difference (V) | DC potential difference (V) |
| --- | --- | --- | --- |
| 2 min | 1.8 | 3 | — |
| 2 min | 1.6 | 3 | — |
| 2 min | 1.4 | 3 | — |
| 2 min | 1.2 | 3 | — |
| 2 min | 1 | 3 | — |
| 2 min | 0.8 | 3 | — |
| 2 min | 0.6 | 3 | — |
| 10 min | 0.6 | 5 | — |
| 1 s | 0.6 | 5 | 1 |
| 5 min | — | — | 2.3 |
| 90 min | 5 | 3.5 | — |
| 10 min | 2.5 | 3.5 | — |
| 10 min | 1.5 | 3.5 | — |
| 10 min | 1 | 3.5 | — |
| 10 min | 0.8 | 3.5 | — |
| 2 min | 0.8 | 4.5 | — |
| 2 min | 0.8 | 5.5 | — |
| 2 min | 0.8 | 6.5 | — |
| 2 min | 0.8 | 7.5 | — |
| 1 s | 0.8 | 5.5 | 2 |
| 10 min | — | — | 2.3 |

2) Second Step: Fixation of the Colloidal Particles P2

An aqueous dispersion was prepared at 3 wt % of colloidal particles P2 consisting of nanospheres (diameter 18 nm) of poly(styrene, divinylbenzene) surface-functionalized with an ion-complexing ligand, Cyclam® (1,4,8,11-tetraazacyclotetiadecane) according to the protocol described in C. Larpent et al., Comptes-rendue de Chimie, 2003, 6, 1275-1283. These particles have a content of cupric ions between 0.2 and 0.3 mmol/g of particles. In this dispersion, the cupric ions were complexed by the ligand Cyclam® fixed on the surface of the nanospheres.

Commercial polystyrene beads (Polybeads) of various sizes 50 nm, 100 nm and 200 nm (in the form of aqueous dispersions at 2.6 wt % of polystyrene beads) were also used as colloidal particles P2. 10 μL of these dispersions were diluted in 1 mL of a solution of hexamethylenediamine (0.1 mol/L) with stirring for 16 hours.

For each dispersion prepared, 50 μl of dispersion was then injected into the cavity of the electrochemical cell using a micropipette. A continuous electric field of −92 V/cm was then applied between the two electrodes for 30 min, in order to induce migration of the particles P2 toward the electrode having the hexagonal array of particles P1-*a* (or P1-*b* or P1-*c*) and fixation thereof on said electrode, between the particles P1-*a* (or P1-*b* or P1-*c*).

3) Third Step: Removal of the Particles P1

After extinction of the field, the cell was opened, washed with distilled water and with ethanol, and then dried. The particles P1-*a* (or P1-*b* or P1-*c*) were then removed from the surface of the electrode using adhesive tape, which was applied on the electrode, leaving an array of microholes of variable diameter, in a polymer matrix consisting of the particles P2.

Figure 3:
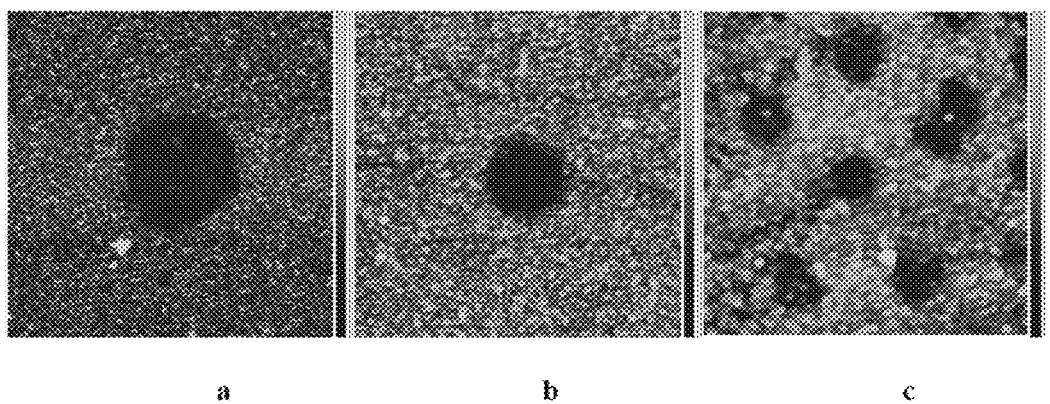
FIG. 3 is an images obtained by atomic force microscopy (AFM) of the surface of the electrodes nanostructured in Example 1, in accordance with one embodiment.

Images obtained by atomic force microscopy (AFM) of the surface of the electrodes nanostructured in this way are shown in the accompanying FIG. 3: holes obtained in the matrix of particles P2 from the mask produced using respectively a) particles P1-*b*: holes of about 1.1 μm in diameter, b) particles P1-*a*: holes of about 630 nm in diameter, and c) particles P1-*c*: holes of about 445 nm in diameter. The scale is identical for these 3 images.

Figure 4:
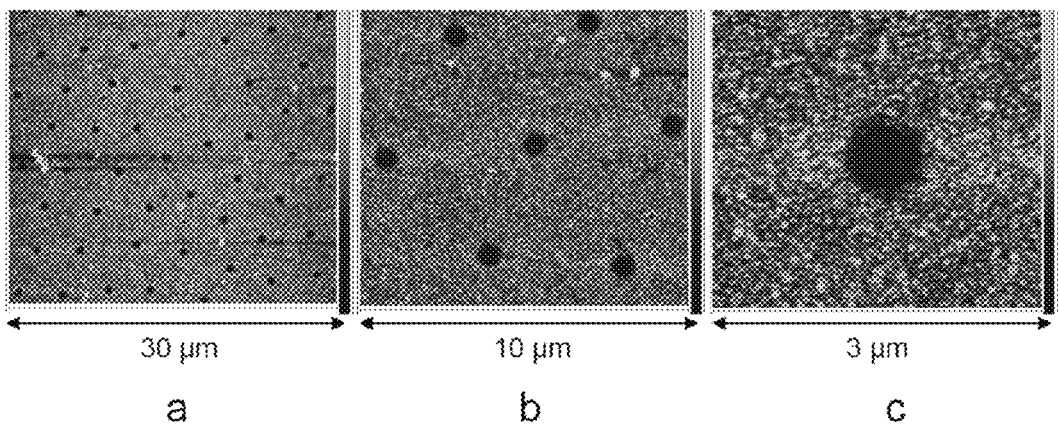
FIG. 4 are images obtained by AFM of the surface of the electrode of Example 1, in accordance with one embodiment.

The accompanying FIG. 4 shows the images obtained by AFM of the surface of the electrode obtained using particles P1-*a* with diameter of 2 μm, then particles P2, at different magnifications: scale a): 30 μm; b): 10 μm and c) 3 μm.

Figure 5:
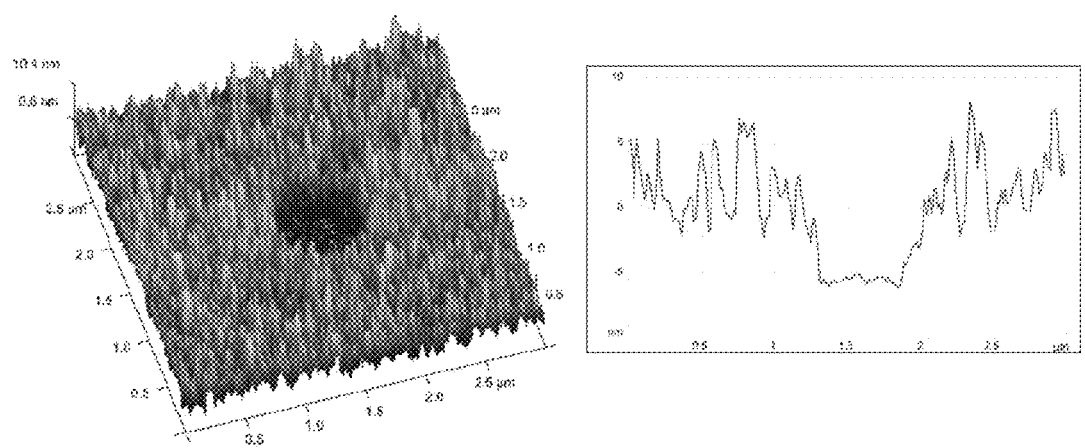
FIG. 5 is a 3D representation of the image of a hole observed by AFM from Example 1. in accordance with one embodiment.

The accompanying FIG. 5 is a 3D representation of the image of a hole observed by AFM.

Figure 6:
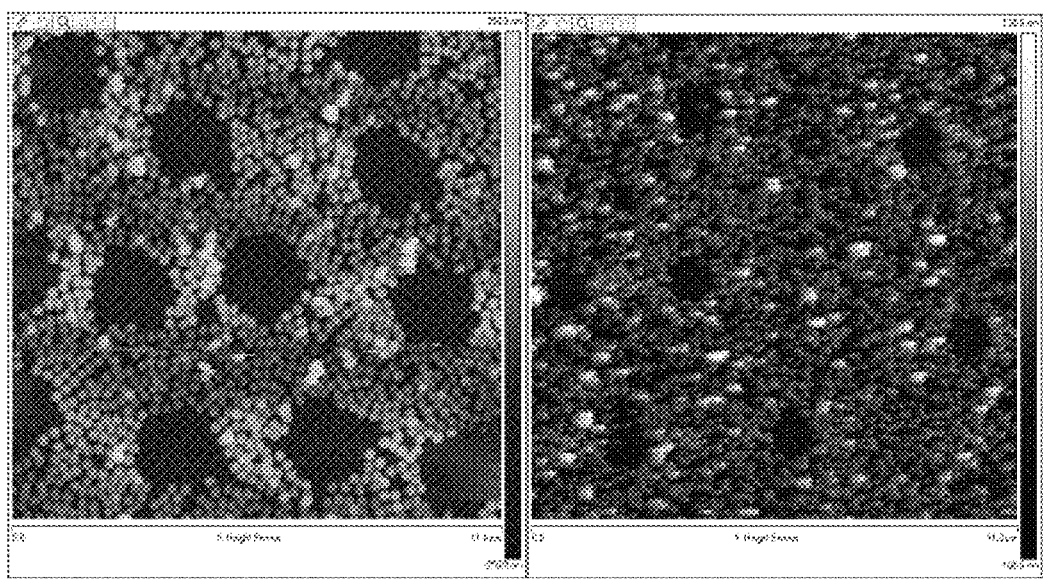
FIG. 6 shows the images obtained by AFM of the surface of the electrode of Example 1 in accordance with one embodiment.
Figure 6:
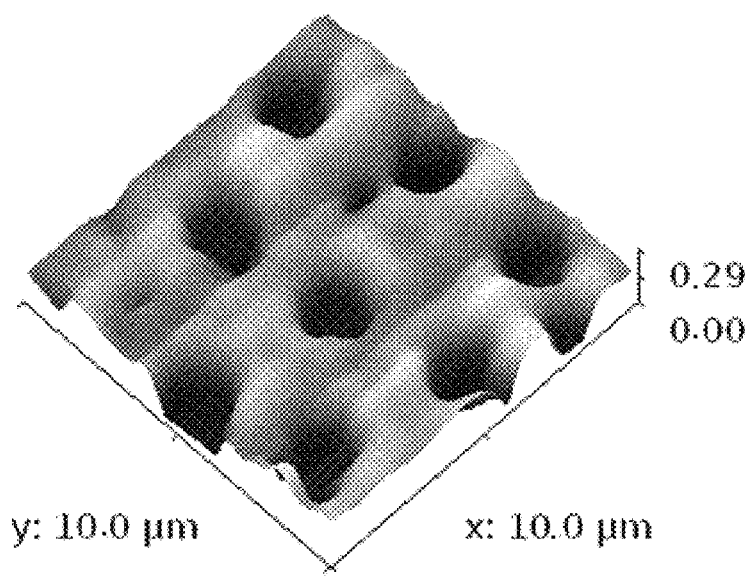

The accompanying FIG. 6 shows the images obtained by AFM of the surface of the electrode obtained using particles P1-*a* with diameter of 2 μm, then commercial polystyrene particles P2 with a size of 200 nm (FIG. 6*a*) and 100 nm (FIG. 6*b*).

These surfaces comprising holes in a matrix consisting of colloidal particles can be heated in order to fuse the particles. A thermal treatment at 175° C. for 35 minutes was carried out for the 200-nm particles P2. The accompanying FIG. 6*c* is a 3D representation of the image obtained by AFM of the surface of the heat-treated electrode.

4) Behavior in Arrays of Microelectrodes

Figure 7:
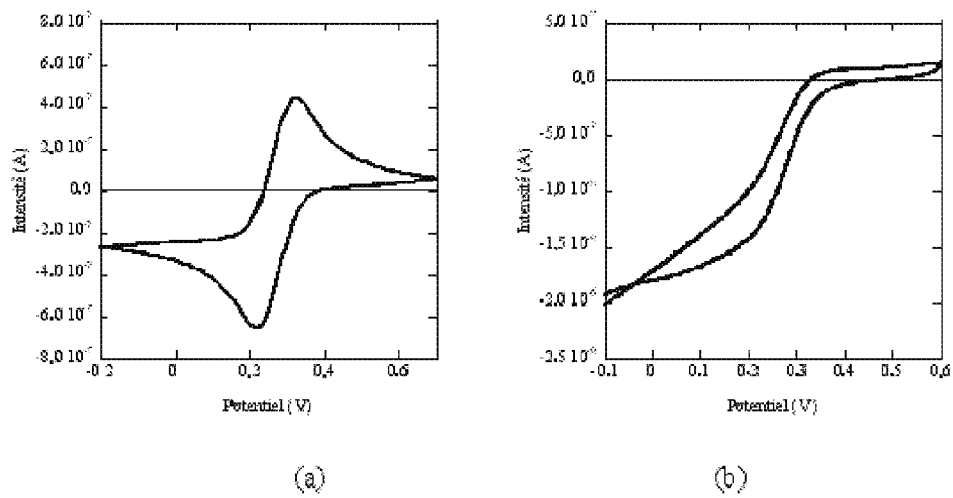
FIG. 7 are voltammograms obtained with a solution of ferricyanide of Example 1, in accordance with one embodiment.

We started with the structured surface based on beads P1-*a*. After fixation of the nanospheres P2 (diameter 18 nm) and removal of the particles P1-*a*, the surface was heat-treated according to the following protocol: temperature rise from room temperature to 220° C. then a plateau at 220° C. for 35 minutes and temperature drop to room temperature in 1 hour. The aim of this thermal treatment was to fuse the nanospheres together in order to make the polymer matrix completely insulating. The surface therefore consists of conducting holes left free by removal of the particles P1-*a*. This heat-treated surface served as the working electrode in a setup with 3 electrodes with Ag/AgCl as reference electrode and a counter-electrode consisting of a platinum grid. The voltammograms obtained with a solution of ferricyanide ($K_3Fe(CN)_6$) at 2 mM and of potassium nitrate ($KNO_3$) at 1M are given in the accompanying FIG. 7, in which the current density J in $A/mm^2$ is a function of the potential E in volts before thermal treatment (FIG. 7*a*) and after thermal treatment (FIG. 7*b*). The scanning rate was 5 mV/s. The voltammogram obtained after thermal treatment has the sigmoidal form characteristic of the electrochemical behavior of an array of micro-electrodes.

Example 2

Preparation of a Nanostructured Surface with a Functional Polymer Matrix According to a Method that is not Part of the Invention In this example, a surface was used that was covered with unorganized particles P2 (particles functionalized with Cyclam® groups). In other words the step of fixation of the particles P1 as described above in example 1 was not carried out. The aim of this example was to show that the particles P2 can be post-functionalized with a biomolecule.

These surfaces were then functionalized with a protein, GFP (acronym of Green Fluorescent Protein), labeled beforehand with a 6-histidine group.

The slide covered with the particles P2 was first treated with an aqueous solution of metal ions at 0.1 mol/L, for example in this case a solution of $NiCl_2$. For this, the slide was placed in a vertical position in a tube containing 25 mL of the solution of $Ni^{2+}$ ions. It was left there for about 1 h, then the slide was rinsed 3 times with ultrapure water and twice with HEPES buffer (pH=7) containing imidazole (20 mM). A protein solution at 0.1 mg/ml of this same buffer solution was prepared and was centrifuged at 20800 g for 5 min at 4° C. in order to remove the protein aggregates. This solution was then deposited with a micropipette on the slide to cover the zone for deposition of particles P2. After incubation for 1 h, the slide was rinsed 5 times with the buffer solution described above.

A surface functionalized with GFP was obtained.

Example 3

Preparation of a Nanostructured Surface with a Metallic Matrix and Demonstration of its Super-Hydrophobic Character A surface nanostructured with copper rings was prepared in this example.

1) First Step: Preparation of a Reverse Mask of Colloidal Particles P1

50 μl of an aqueous dispersion of particles P1 at 0.1 wt %, consisting of polystyrene beads with a diameter of 2 μm sold under the trade name Polybeads® by the company Polysciences, Inc. and already functionalized with sulfate groups, was introduced into the cavity of an electrochemical cell C1 using a micropipette.

This dispersion was left to sediment for 20 minutes in a sinusoidal electric field (frequency: 5 kHz, 120 V/cm). A sequence similar to that shown in Table I of example 1 above was then applied for organizing the particles P1 and immobilizing them on the positive electrode in a hexagonal array. The time for immobilizing the particles P1 (last line of the table) was fixed at 5 mm or 20 minutes depending on the experiment.

2) Second Step: Fixation of the Colloidal Particles P2

A dispersion of particles P2 at 500 mg/ml consisting of multilamellar vesicles containing cupric ions was prepared by simple equal-weight mixing of an aqueous solution of cupric sulfate (0.68 M) and a surfactant of the tallow oil ethoxy late type sold under the trade name Genamin T020® by the company Clariant, and having the particular feature that it self-organizes in the form of multilamellar vesicles in the presence of an aqueous phase.

50 μl of this dispersion was introduced into the cavity of the electrochemical cell, then a continuous electric field of ~92 V/cm was applied for 20 min, in order to attract the vesicles of surfactant containing the cupric ions, which will be reduced on the electrode. The particles P1 thus underwent 20 minutes of immobilization.

The same experiment was repeated in two other electrochemical cells (C2 and C3), using exactly the same dispersions of particles P1 and of particles P2, but applying the following parameters:

electrochemical cell C2: 20 minutes of immobilization of the particles P1 and 5 minutes of attraction of the particles P2;

electrochemical cell C3: 5 minutes of immobilization of the particles P1 and 20 minutes of attraction of the particles P2;

electrochemical cell C4: 5 minutes of immobilization of the particles P1 and 130 minutes of attraction of the particles P2.

3) Third Step: Removal of the Particles P1 and P2

Extinction of the field causes detachment of the vesicles P2 (empty of copper) from the electrode. The cells were then opened, washed with water and with ethanol to remove the vesicles P2 and any trace of organic matter, and then dried.

The particles P1 were then removed from the surface of the electrodes in each of the cells C1 to C3 using adhesive tape, which was applied on the electrode, leaving an array of copper micro-rings. For cell C4, the slide was immersed in a solution of pure tetrahydrofuran for 20 min, and then rinsed with THF. It was again immersed for 20 min in the solution of THF and then rinsed with THF and with ethanol before being dried.

Figure 8:
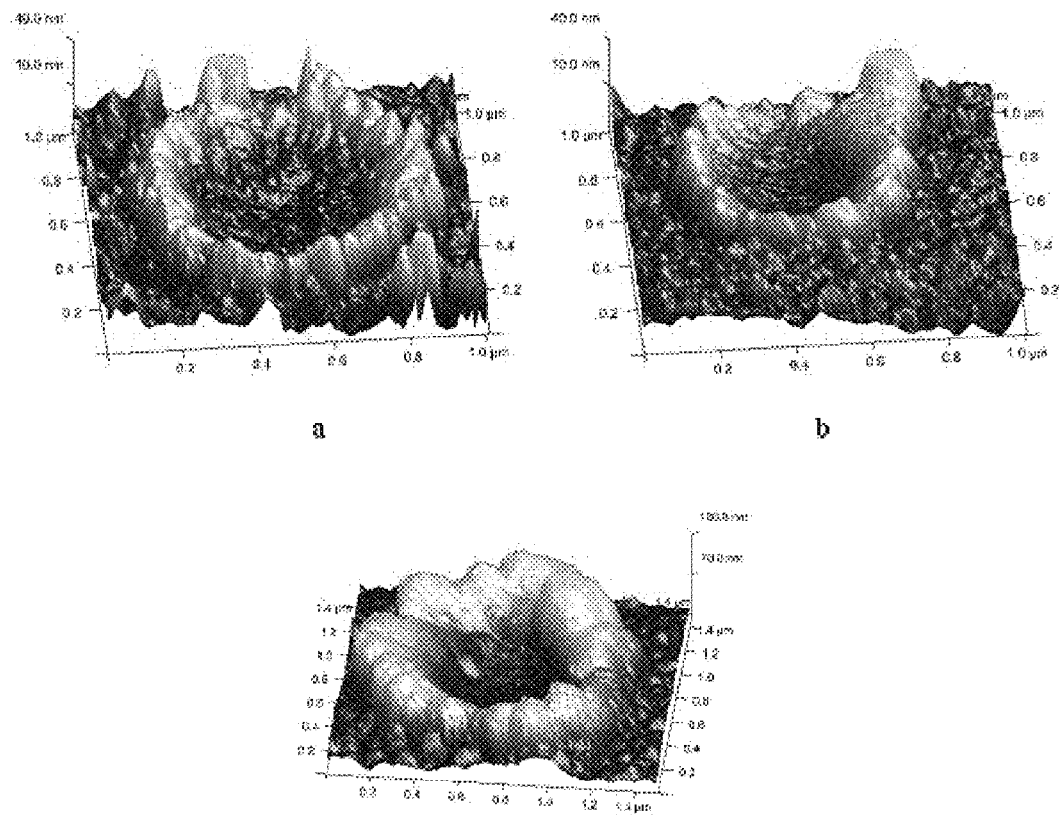
FIG. 8 is a 3D representation of the images obtained by atomic force microscopy of the metal rings from Example 3, in accordance with one embodiment.

FIG. 8 is a 3D representation of the images obtained by atomic force microscopy of the metal rings formed on the surface of each of the electrodes: a) electrochemical cell C1, b) electrochemical cell C2; c) electrochemical cell C3.

It can be seen in this diagram that the morphology of the copper rings can be modulated as a function of the duration of application of the electric fields during migration and fixation of the particles P1 and P2.

Figure 9:
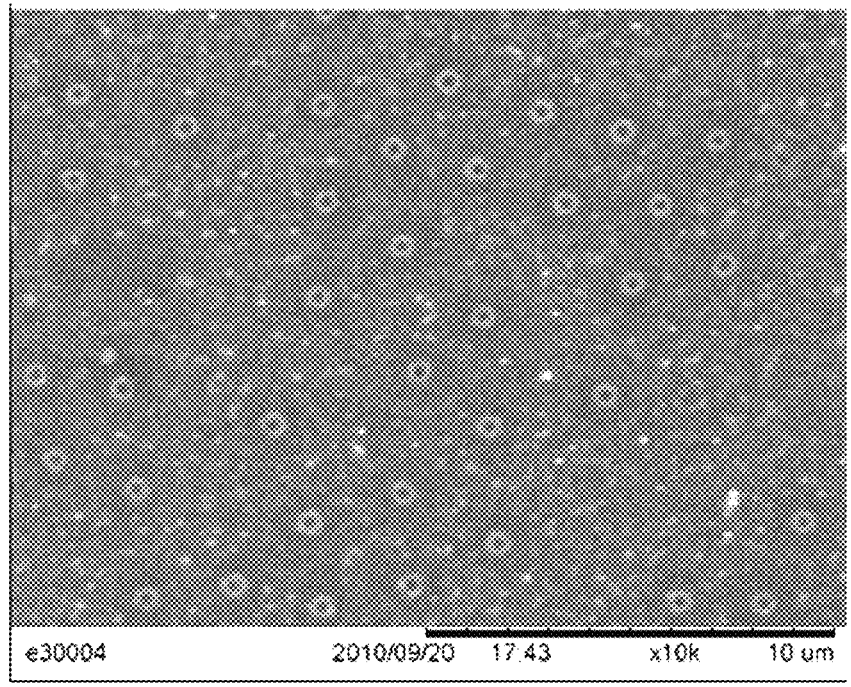
FIG. 9 is a photograph taken by scanning electron microscopy (SEM) of the surface of the nanostructured electrode of cell C2 of Example 3, in accordance with one embodiment.

The accompanying FIG. 9 is a photograph taken by scanning electron microscopy (SEM), magnification ×3500, of the surface of the nanostructured electrode of cell C2.

Figure 10:
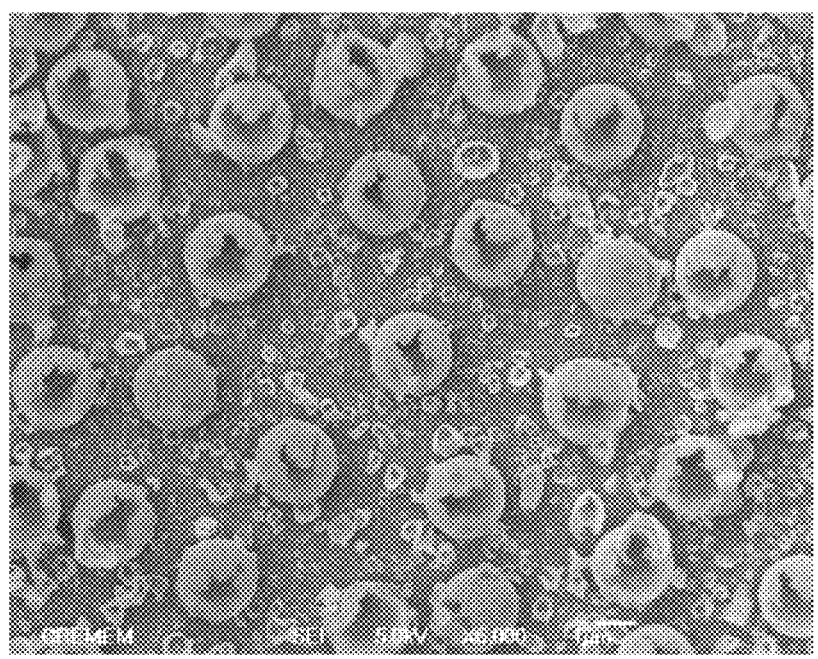
FIG. 10 is a photograph taken by scanning electron microscopy (SEM) of the surface of the nanostructured electrode of cell C4 of Example 3, in accordance with one embodiment.

The accompanying FIG. 10 is a photograph taken by scanning electron microscopy (SEM), magnification ×5000, of the surface of the nanostructured electrode of cell C4. In this case organized "shells" of copper are obtained.

4 Demonstration of the Super-Hydrophobic Character of the Organized Copper Surfaces The static contact angle of the surfaces formed for different times of reduction and for one and the same time of immobilization of 5 min was measured, in particular on the surfaces obtained from C3 corresponding to the 20 min point and C4 corresponding to 130 min. Measurement consists of depositing a drop of ultrapure water using a syringe on the surface whose contact angle we wish to measure. A photograph of the drop is taken at grazing incidence. After digitization of the contour of the drop, the angle made by the tangent to the drop at the solid-liquid-gas triple point and the solid surface is calculated. This angle is called the contact angle ($\theta$). This contact angle is controlled by the time of application of the field permitting reduction of the copper.

Figure 11:
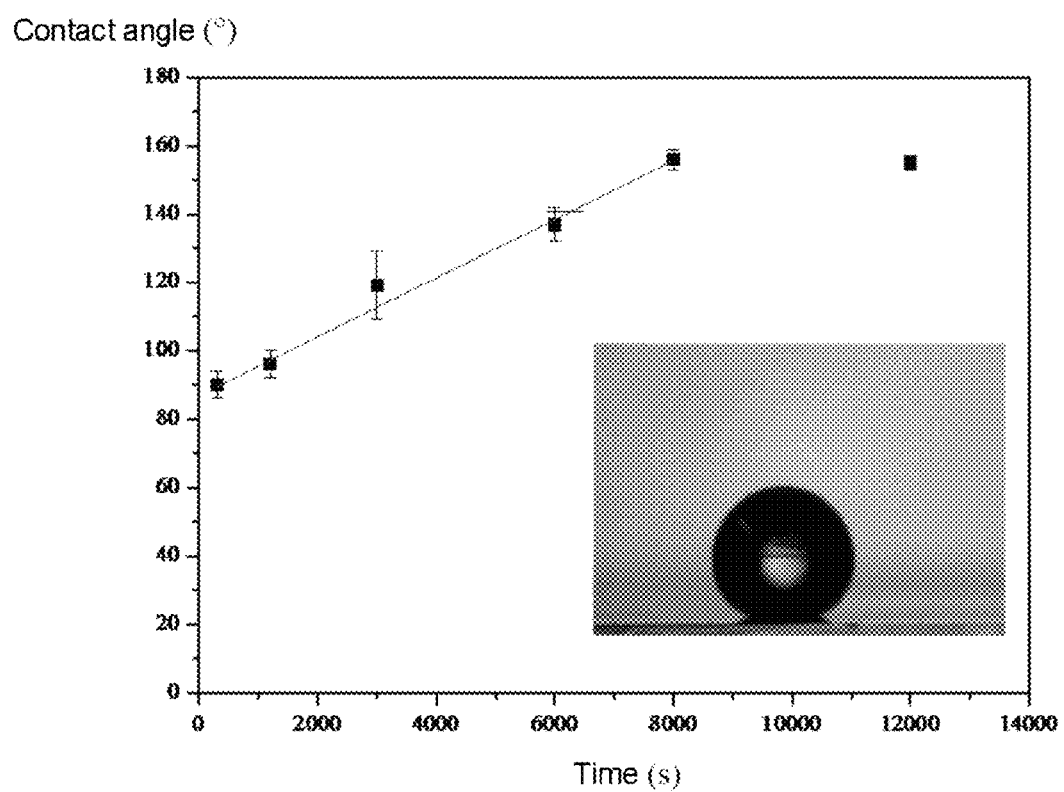
FIG. 11 is a plot of the value of the contact angle (in °) as a function of the time of attraction of the particles P2 (in seconds) from Example 3, in accordance with one embodiment.

FIG. 11 plots the value of the contact angle (in °) as a function of the time of attraction of the particles P2 (in seconds). A photograph showing the wetting of the structured surface for 8000 seconds by a drop of water is also shown.

Its maximum value is 160° for the surfaces tested, obtained according to the method of the invention, without any hydrophobization. For comparison, the highest value found in the literature for copper surfaces deposited under a continuous electric field is 138° (X Liu et al., Thin Solid Films, 2010, 518, 3731-3734).

Accordingly, these results demonstrate the super-hydrophobic character of the surfaces produced by the method according to the invention.

The invention claimed is:

1. A method of preparing a surface micro- or nanostructured by organized inorganic and/or organic micro- or nanostructures, said method employing colloidal particles and an electrochemical cell having a working electrode and a counter electrode, said electrodes being plane-parallel relative to one another, with conducting faces opposite each other, and separated from one another by an insulating spacer having at least two openings and delimiting a free volume (V) between the two electrodes, said method comprising the steps of:
   i) preparing a dispersion of electrically charged, monodispersed hydrophilic colloidal particles (particles P1) in an aqueous phase, said particles P1 having a size greater than or equal to about 0.5 µm;
   ii) preparing a dispersion of electrically charged colloidal particles (particles P2) in an aqueous phase, said particles P2 having a size less than that of the particles P1, being of the same electric charge as the particles P1, and optionally containing at least one electrochemical species;
   iii) introducing the dispersion of particles P1 into the free volume (V) through one of the openings in the spacer;
   iv) causing the particles P1 to migrate toward the surface of the counter electrode of charge opposite to that of the particles P1 (working electrode), by applying a sinusoidal electric field perpendicularly to said electrodes,
   v) applying a sinusoidal electric field of decreasing frequencies at constant potential, to cause aggregation of the particles P1 on the surface of the working electrode;
   vi) gradually increasing the frequency of the sinusoidal electric field until a crystal lattice is obtained consisting of a monolayer of particles P1 on the surface of the working electrode;
   vii) immobilizing the particles P1 in a form of said crystal lattice, by superimposing, on the sinusoidal electric field, a continuous electric field of sign opposite to the charge of the particles P1, then extinguishing the sinusoidal electric field while maintaining the continuous electric field for a sufficient time to cause adhesion of the particles P1 on the surface of the working electrode;
   viii) introducing the dispersion of particles P2 into the free volume V of the electrochemical cell, and applying a continuous electric field for a sufficient time to cause migration and fixation of the particles P2 on the free surface of the working electrode on which the immobilized particles P1 has formed, and when the particles P2 contain an electrochemical species, oxidation or reduction of said electrochemical species on the surface of the working electrode;
   ix) removing the particles P1 from the surface of the working electrode to obtain a surface that is nanostructured with the particles P2 or with the oxidized or reduced electrochemical species supplied by the particles P2.

2. The method as claimed in claim 1, wherein the particles P1 are selected from spherical particles with average diameter between 0.5 µm and 5 µm.

3. The method as claimed in claim 1, wherein the quantity of particles P1 in the dispersion varies from 0.1 to 0.6 wt %.

4. The method as claimed in claim 1, wherein the particles P2 are selected from the group consisting of filled polymers having at least one organic function having affinity for the working electrode, metal particles surface-functionalized with at least one organic function having affinity for the working electrode, and the carbon nanotubes surface-functionalized with at least one organic function having affinity for the working electrode.

5. The method as claimed in claim 1, wherein the particles P2 are selected from either one of lamellar vesicles based on at least one surfactant and containing said electrochemical species.

6. The method as claimed in claim 5, wherein the electrochemical species contained in the vesicles is selected from either one of metal ions and redox monomers.

7. The method as claimed in claim 5, wherein the lamellar vesicles have a size between 0.1 µm and 1.5 µm.

8. The method as claimed in claim 1, wherein the electric field applied during step iv) between the two electrodes varies from 100 to 150 V/cm and the crystal lattice of particles P1 is then a hexagonal array.

9. The method as claimed in claim 1, wherein the electric field applied during step iv) between the two electrodes varies from 200 V/cm to 250 V/cm and the crystal lattice of particles P1 is then an array in a form of chains having on average of 3 particles P1.

10. The method as claimed in claim 1, wherein the crystal lattice of particles P1 obtained on the surface of the working electrode at the end of step vi) is in a form of a compact hexagonal array, a noncompact hexagonal array or else in a form of an array of triplets of particles P1 isolated from one another, said triplets being arranged in rods and/or in triangles.

11. The method as claimed in claim 1, wherein said method further comprises, after step viii) of fixation of the particles P2, an additional step of functionalization of the particles P2 with a biomolecule of interest.

12. The method as claimed in claim 11, wherein said additional step of functionalization is carried out either just after step viii) of fixation of the particles P2 and before step ix) of removal of the particles P1, or after step ix) of removal of the particles P1.

13. The method as claimed in claim 11, wherein the biomolecules of interest are selected from the group consisting of proteins bearing a histidine label, a streptavidin ligand or a biotin ligand, antigens and molecules of nucleic acids.

* * * * *